United States Patent
Al-Mahrous et al.

(10) Patent No.: US 7,189,319 B2
(45) Date of Patent: Mar. 13, 2007

(54) AXIAL CURRENT METER FOR IN-SITU CONTINUOUS MONITORING OF CORROSION AND CATHODIC PROTECTION CURRENT

(75) Inventors: Husain M. Al-Mahrous, Dhahran (SA); Darrell R. Catte, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 406 days.

(21) Appl. No.: 10/782,604

(22) Filed: Feb. 18, 2004

(65) Prior Publication Data
US 2005/0178673 A1   Aug. 18, 2005

(51) Int. Cl.
*C23F 13/04* (2006.01)

(52) U.S. Cl. .................. 205/726; 205/725; 205/728; 205/729; 205/730; 205/734; 205/740; 204/196.03; 204/196.04; 204/196.07; 204/196.11; 204/196.21; 204/196.26; 204/196.36; 204/196.37

(58) Field of Classification Search ............... 205/725, 205/726, 728, 729, 730, 734, 740; 204/196.36, 204/196.02, 196.37, 196.03, 196.04, 196.05, 204/196.06, 196.07, 196.11, 196.21, 196.26
See application file for complete search history.

(56) References Cited

U.S. PATENT DOCUMENTS

| | | | |
|---|---|---|---|
| 1,608,709 A | 11/1926 | Mills | |
| 1,927,664 A | 9/1933 | Karcher | |
| 2,085,664 A | 6/1937 | Karcher | |
| 2,153,802 A | 4/1939 | Jakosky | |
| RE21,102 E | 5/1939 | Jakosky | |
| 2,247,417 A | 7/1941 | Silverman | |
| 2,249,769 A | 7/1941 | Leonardon | |
| 2,364,957 A | 12/1944 | Douglas | |
| 2,557,168 A | 6/1951 | Arps | |
| 2,875,142 A | 2/1959 | Landers | |
| 2,917,704 A | 12/1959 | Arps | |
| 3,024,651 A | 3/1962 | McGlasson | |
| 3,115,942 A | 12/1963 | Arps | |
| 3,714,004 A | 1/1973 | Riggs, Jr. | |
| 4,164,257 A * | 8/1979 | Anthony et al. ............. | 166/113 |
| 4,526,667 A * | 7/1985 | Parkhurst et al. ...... | 204/196.06 |
| 4,578,675 A | 3/1986 | MacLeod | |
| 4,625,173 A | 11/1986 | Wisler | |
| 4,713,158 A | 12/1987 | Lambert | |
| 4,786,388 A * | 11/1988 | Tatum, Jr. .............. | 204/196.21 |
| 4,794,322 A | 12/1988 | Davies | |
| 4,837,518 A | 6/1989 | Gard | |
| 4,857,831 A | 8/1989 | Davies | |
| 4,942,361 A | 7/1990 | Gast | |
| 5,463,320 A | 10/1995 | Bonner | |
| 5,509,490 A | 4/1996 | Paske | |
| 5,533,572 A | 7/1996 | Brady | |
| 5,627,749 A | 5/1997 | Waterman | |
| 6,131,659 A | 10/2000 | Johnson | |
| 6,224,742 B1 * | 5/2001 | Doniguian .................. | 205/724 |
| 6,249,122 B1 | 6/2001 | Vail, III | |

(Continued)

*Primary Examiner*—Bruce F. Bell
(74) *Attorney, Agent, or Firm*—Abelman, Frayne & Schwab

(57) ABSTRACT

First and second axial current meters (ACM) are mechanically connected to a well casing just above and below a corrosive zone and a master axial current meter (MACM) is connected to the casing at the earth's surface, the MACM periodically obtaining measurements of axial current from the ACMs to determine how much cathodic protection current is to be applied to the casing to avoid corrosion.

24 Claims, 5 Drawing Sheets

U.S. PATENT DOCUMENTS

2002/0135348 A1* 9/2002 Thomas et al. ............ 324/71.2
2003/0074162 A1* 4/2003 Fourie et al. ............... 702/188
2003/0201100 A1* 10/2003 Al-Ramadhan .......... 166/242.4
2004/0057174 A1* 3/2004 Al-Mahrous ................. 361/57

* cited by examiner

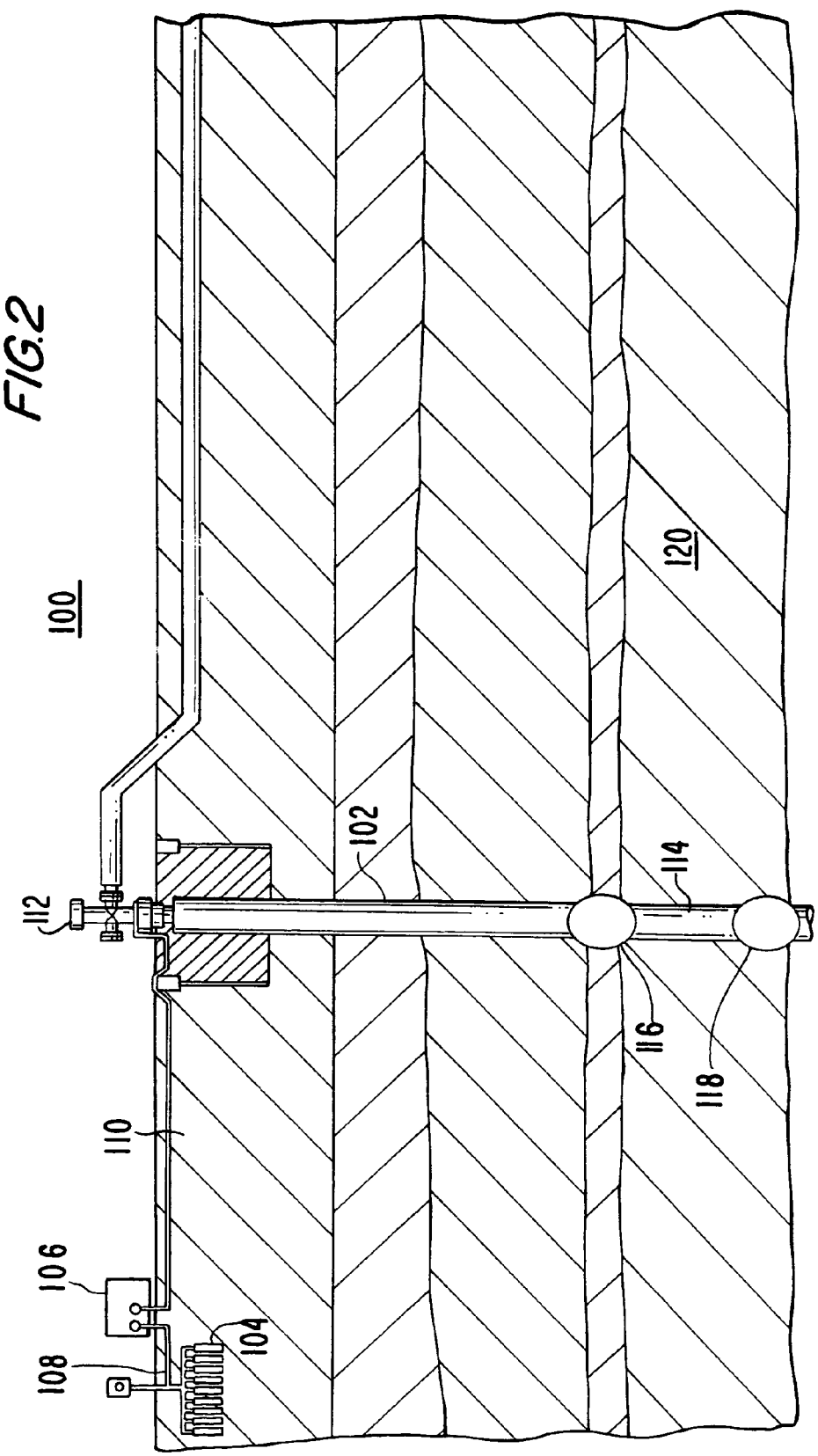

AXIAL CURRENT METER FOR IN-SITU CONTINUOUS MONITORING OF CORROSION AND CATHODIC PROTECTION CURRENT

FIELD OF THE INVENTION

This invention relates to apparatus and methods for monitoring the level of cathodic protection and the long line corrosion current at a specific location or within a specific area on buried metallic pipelines and well casings.

BACKGROUND OF THE INVENTION

Underground or submerged metal structures such as well casings and pipelines need a means of protection against soil-side corrosion. Cathodic protection (CP) is a well-known electrochemical method that has proved to be an effective method of mitigating external corrosion on well casings and pipelines.

Cathodic protection for well casings and long pipelines is typically applied in an impressed current configuration, e.g., from an external DC power supply. Impressed current cathodic protection involves the introduction of a conductive material (typically cast iron rods) buried in the ground and electrically connected to the positive (anode) terminal of an external DC power supply. The negative (cathode) terminal of the power supply is connected to the structure to be cathodically protected.

In a perfect cathodic protection system, only the anode's surface corrodes. The transfer of electrical current by a DC power supply through the electrolyte from the anode to the cathode results in corrosion of the anode and overcomes the natural corrosion currents on the cathode, e.g., a pipeline or well casing in this application. Consequently, the anodes require periodic replacement, but the structure of the well casing or pipeline operates for its required life without need for replacement due to corrosion.

FIG. 1 illustrates the setup of a conventional impressed current CP system 10 for a well casing 12. As shown therein, an anode bed 14 is buried in the ground and a cathodic protection DC power supply 16 is connected to the anode bed 14 by a positive cable 18, and to the well casing by a second negative cable 20 at the well head 22 near the ground surface. The cathodic protection DC power supply must provide a sufficient amount of cathodic protection current to protect the portion 24 of the well casing 12 passing through the corrosive zone 26.

Wireline logging tools are commonly used to measure axial current in well casings. The axial currents can be caused by natural corrosion current, by cathodic protection current, or by a combination of both. The measurements of axial currents in a well casing are used to identify anode and cathodic zones and, with cathodic protection applied are used to determine the amount of cathodic protection current required from the DC power supply to offset the natural corrosion currents in the anodic zones.

A common practice in the prior art has been to conduct several logs in a problematic field to generalize the area of corrosion and the amount of cathodic protection required from the DC power supply. The assumption that all wells in a given area are sufficiently similar and that all require the same cathodic protection current is a practical necessity due to the cost and impracticality of conducting an axial current log on every well.

The corrosive areas may have been defined through failure histories, or possibly through wire line logging.

It is an object of the present invention to provide a cost effective and practical alternative for determining the amount of cathodic protection required to protect a new well in a field where the corrosive formations have been reasonably well defined.

Another object of the invention is to provide a permanent installation that will provide a reliable method of monitoring the cathodic protection requirements.

Yet another object of the invention is to provide a method and apparatus for permanent in-situ monitoring of corrosion and cathodic protection current.

SUMMARY OF THE INVENTION

The above and other objects are achieved by the present invention which, in one embodiment, is directed to an apparatus for determining an amount of cathodic protection current to be applied to an underground metallic structure in contact with an underground earth formation, the structure having an extended underground length extending through a corrosive zone of the formation.

The apparatus comprises a first axial current meter (ACM) mechanically connected to the structure at a first underground depth substantially just above the corrosive zone for measuring a first axial current flowing through the structure at the first depth, a second axial current meter mechanically connected to the structure at a second underground depth substantially just below the corrosive zone for measuring a second axial current flowing through the structure at the second depth, and a master axial current meter (MACM) connected to the structure substantially near the earth's surface. A connecting structure is also provided for carrying signals between the MACM and each of the first and second ACMs.

In accordance with the present invention, the MACM includes a control for operating over a selected limited time period to periodically obtain a series of first measurements of the first axial current from the first ACM and a series of second measurements of the second axial current from the second ACM, each second measurement being obtained at substantially the same time as a corresponding first measurement, and the MACM provides information based on the first and second measurements for determining an amount of cathodic protection current to be applied to the structure to avoid corrosion of the structure in the corrosive zone.

These and other objects, features and advantages of the present invention will be apparent from the following detailed description of the preferred embodiments taken in conjunction with the following drawings, wherein like reference numerals denote like elements.

BRIEF DESCRIPTION OF THE DRAWINGS

FIG. 2 is an illustration of a system for supplying cathodic protection current to a well casing in accordance with an embodiment of the present invention.

DETAILED DESCRIPTION OF THE PREFERRED EMBODIMENTS

The present invention is embodied in method and apparatus that provide clear confirmation and quantification of the corrosive zones, and optimize the rectifier output current. This is achieved by measuring the voltage drop caused by the flow of DC axial corrosion current in the casing, and by utilizing this data to determine how much CP is required for a particular well casing.

In addition, for a well that has been determined to require CP, by an embodiment of the invention (or any other logging tool), the present invention also can be used to optimize the current requirement to cathodically protect the well down through the corrosive zone by measuring the voltage drop caused by CP axial current flow and then by adjusting the rectifier current output to optimize the protection level.

For buried pipelines, long-line corrosion can be detected and CP current can be optimized utilizing the method and apparatus of the present invention. For submerged pipelines, only CP current optimization can be so achieved.

The method of the present invention generally utilizes two different devices: (1) an axial current meter (ACM) which measures axial current passing through the metal structure at its location, and (2) a master axial current meter (MACM) which communicates and collects the data from a number of such ACMs placed at selected locations along the metal structure. Preferably two ACMs are mounted so that they fall just on either side of the corrosive zone.

In the following discussion, the method of the present invention will be described in the context of CP protection of a well casing. It will be understood, of course, that other metal structures may be evaluated and protected by the present invention, and that the appropriate modifications to such other structures will be apparent to those of ordinary skill in the art.

In this context, each ACM measures axial current passing through the metal casing at a down hole sub, and the MACM communicates and collects the data from a number of such ACMs placed at selected locations along the metal structure. In one preferred embodiment, two ACMs are mounted on two subs to be added to the casing so that the subs fall just below and above the corrosive zone.

Figure 1:
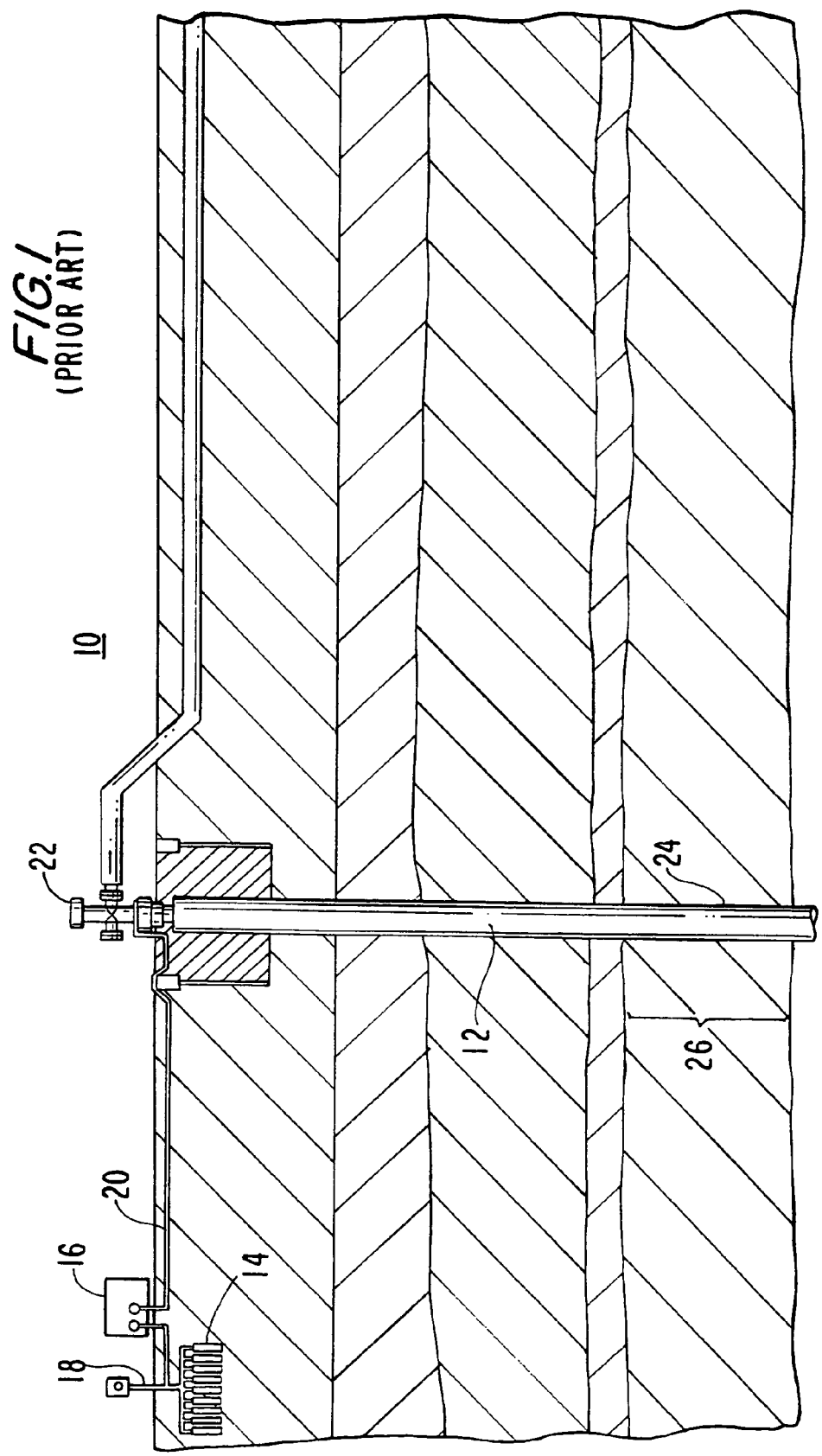
FIG. 1 is an illustration of a conventional system of the prior art for supplying cathodic protection current to a well casing.

FIG. 2 illustrates the setup of a CP current system 100 for a well casing 102 in accordance with this preferred embodiment. As in the conventional system 10 of FIG. 1, an anode bed 104 is buried in the ground near the well casing 102 and the CP rectifier 106 has its positive cable 108 connected to the anode bed 104 and its negative cable 110 connected to the well casing 102 at the well head 112 near the ground surface. The CP rectifier 106 must provide a sufficient amount of CP current to protect the portion 114 of the well casing 102 passing through a corrosive zone.

In FIG. 2, however, two ACMs 116, 118 are provided at first and second locations on the well casing 102. The locations for the ACMs 116, 118 are predetermined to cover the formations below, through and above a known corrosive zone 120 (or what is thought to be a corrosive zone in a new field). Thus, ACM 116 is located just above the corrosive zone 120 and ACM 118 is located just below the corrosive zone 120.

Figure 4:
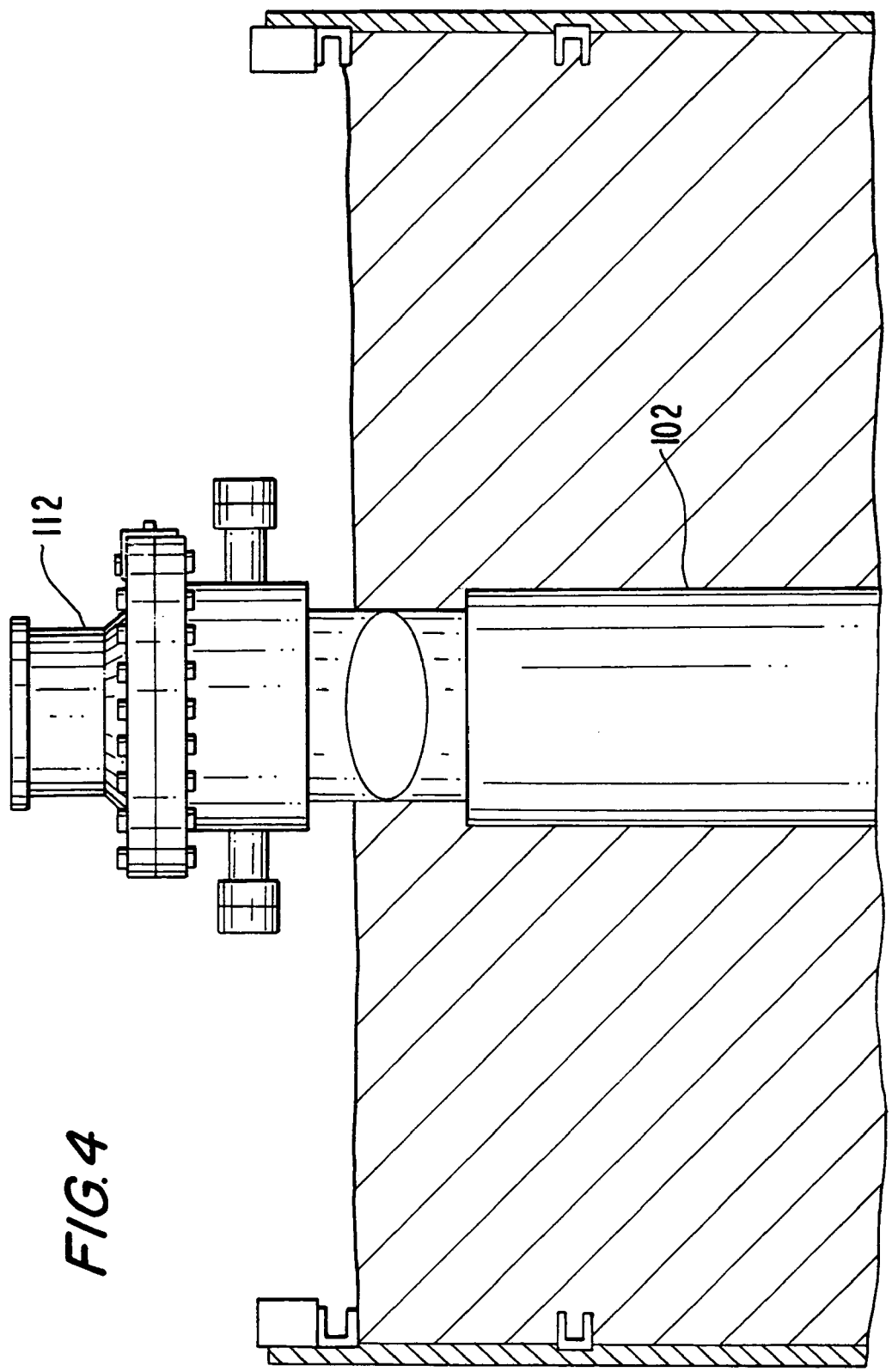
FIG. 4 is an illustration of the master axial current meter mounted on the well casing.

As shown in FIG. 4, the MACM 122 is located at the surface, below the well head 112, so that it may be easily accessed.

Figure 3C:
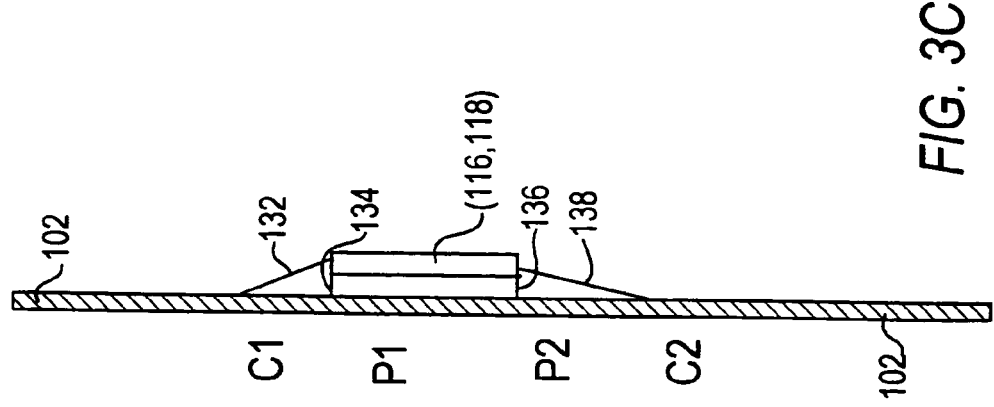
FIG. 3 is a schematic illustration of the mechanical mounting of each axial current meter on the well casing.
Figure 3B:
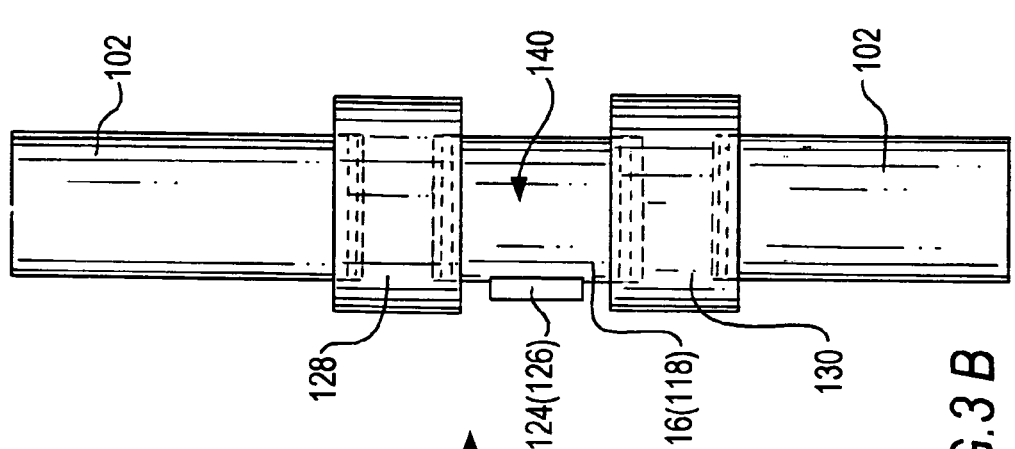
Figure 3A:
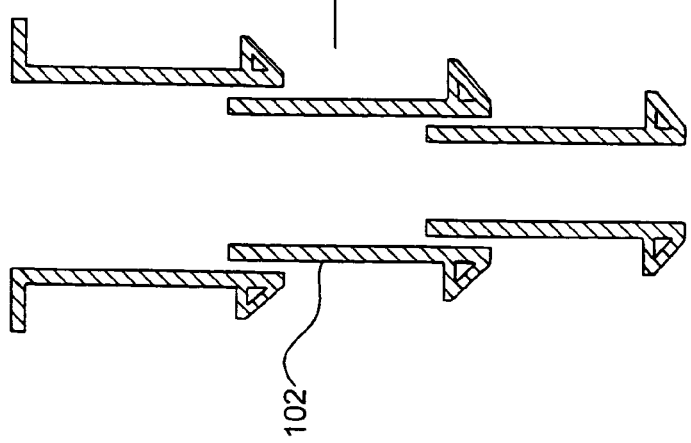

FIG. 3 schematically illustrates that ACM 116 is connected to the well casing 102 by being mounted on a sub 124 at its location. ACM 118, which is identical to ACM 116, is correspondingly connected to the well casing 102 by being mounted on a sub 126 at its respective location. In accordance with known techniques, each of the subs 124, 126 is mounted in the casing 102 by means of upper and lower collars 128, 130.

ACM 116 (and ACM 118) advantageously has four cables 132, 134, 136, 138 tack welded or brazed to the sub joint 140 of the casing 102, insulated off from the sub 124, and terminated to the four terminals C1, P1, C2, P2 of the ACM 116. The ACM 116 must be manufactured and mounted on a sub so that it is fixed in place, secured from any damage during the drilling operation and does not interfere with or obstruct the drilling activities.

Figure 6:
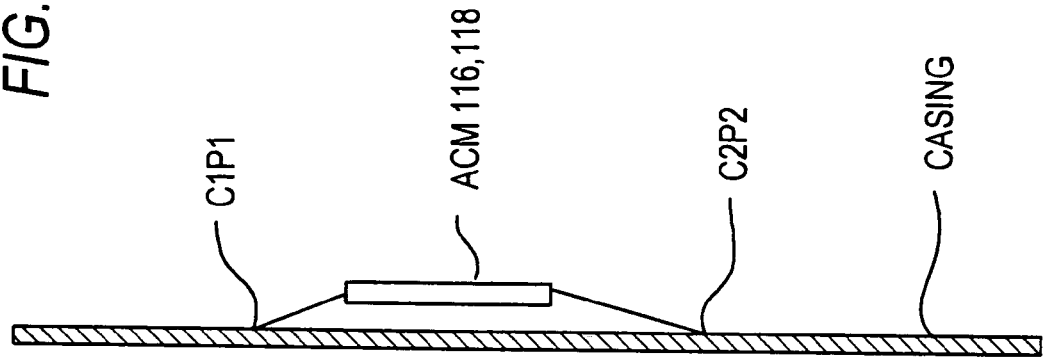
FIG. 6 is an illustration of the two pin method of axial current measurement.
Figure 5:
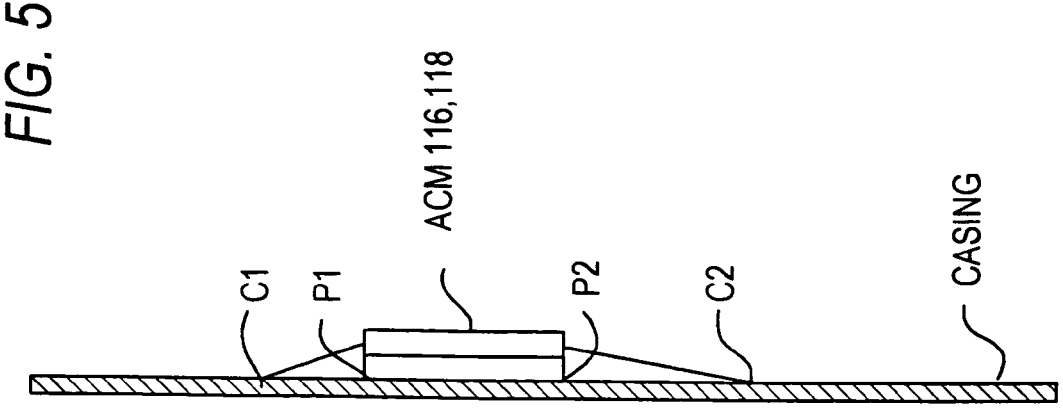
FIG. 5 is an illustration of the four pin method of axial current measurement.

With these four cable connections, each ACM 116, 118 utilizes either the conventional four-pin method shown in FIG. 5 or the conventional two-pin method illustrated in FIG. 6 with C1 shorted to P1 and C2 shorted to P2 to measure the resistance of the casing 102 where the respective sub is added. This measurement is generally conducted by injecting AC current from an outer terminal (C1 and C2) of the ACM and measuring the voltage drop detected by the inner terminals (P1 and P2) on the sub, caused by casing axial AC current flow. Using Ohm's Law, the ACM calculates the resistance of the casing section. The axial current here is an AC signal that is not affected by natural corrosion current or CP current, which are both DC.

More specifically, the four-pin method shown in FIG. 5 uses AC current injected into the casing 102 from outer terminal C1 and collected by outer terminal C2. The voltage difference caused by the current flow is measured, as is the resistance of the casing 102 using Ohm's Law. In a static log, the axial DC casing current is measured by two ACMs to determine if the zone in between is corrosive. In a polarized log, the axial casing current is measured after CP has been applied to polarize the casing in order to determine the level of protection achieved and to optimize the CP system.

The two-pin method is the employment of a resistance meter having the four terminals P1, C1, P2, C2 to measure the resistance of a circuit by shorting terminals P1 with C1 and P2 with C2. As shown in FIG. 6, the resistance between the two terminals C1P1 and C2P2, which includes the wire resistances, is measured. The wire resistances can be obtained in shop tests. Otherwise, the procedure is generally the same as in the four-pin method.

This invention is advantageously applicable to new coated well casings, with the casing body being used as a communication medium between the MACM and downhole ACMs. It can also be used for new bare or uncoated well casings with a cable to establish communication between the MACM and the ACMs.

Each ACM 116, 118 does not need to last for more than the lifetime of the battery system after well casing completion, because the appropriate CP current can be determined and applied in this period. Therefore, it can be manufactured to last for that period and supplied with a battery to last only that long. For well casings, each ACM should be equipped with a thermometer (not illustrated) to measure downhole temperature at the respective depths and to check against the calculated casing resistance values accordingly.

In a further development, each ACM can also be equipped with a thermoelectric cell that utilizes the downhole heat to self generate electrical power for supplying its own electronics.

For pipelines, a portable MACM can be used and equipped with batteries that will power the pipeline ACM units and activate them to instantly collect and transmit axial current to the MACM.

Each ACM can be operated to obtain the following measurements:

1. Static Measurement

If CP has not yet been applied to the casing, the ACM measures the voltage drop caused by axial corrosion current flow in the casing and determines the value of that current. After well completion, the MACM will send a signal through the coated casing (or through a cable if the casing is bare) to remotely activate one ACM unit at a time. The activated ACM will wake up, indicate its depth, measure the voltage drop caused by axial DC corrosion current flow through the casing (if any), transmit the value to MACM and go back to sleep, in order to prolong the life of the battery. The same operating procedure applies to the other ACM.

The MACM collects and analyzes the data and plots a graph of current vs. depth based on the data collected by the two ACMs. If both ACM units agree that there is no measured voltage drop along the casing (no axial corrosion current is detected), this means that there is no long-line corrosion activity taking place along the casing and that CP may not be required.

On the other hand, if the lower ACM indicates upward axial corrosion current while the upper ACM detects downward axial corrosion current, then this suggests that the section of the casing between the two subs is discharging current to the formation (long-line corrosion is active), and therefore CP is required. In this case, an assumed amount of CP is applied to polarize the casing, and another polarized measurement is conducted to ensure that the entire casing receives sufficient protection. The CP rectifier current output will be optimized to cover only the casing down through the deepest reachable corrosive (anodic) zone.

2. Polarized Measurement

Conversely, if CP has been applied prior to the measurement, the ACM measures the voltage drop caused by axial CP current flow in the casing and determines the value of the protection current required. Following the same procedure for the static measurement described above, the exact amount of CP current needed to adequately protect a casing (making it a big cathode) is determined and optimized. The MACM will collect and analyze the data and plot a graph of axial CP current vs. depth based on the values gathered from the two ACMs. If the ACM units confirm that there is a measured voltage drop along the casing caused by upward axial CP current collected on the casing from the formation, this means that the slope will be positive and that sufficient CP is being received. On the other hand, if the applied CP is not sufficient, the slope will be negative at the bottom of the corrosive zone, indicating that additional CP is required.

Another application of the present invention is for pipeline axial corrosion current measurement before the application of CP. The ACMs can be added to a buried pipeline at predetermined locations along the line to investigate if long-line corrosion was taking place. Long-line corrosion is likely to happen on pipelines where a long section of the line is buried in a low resistivity soil, while the next section is buried in a more resistive soil.

After CP application, the method of the present invention can be used to optimize axial CP current based on predetermined current density requirements.

A similar concept applies to submerged pipelines, with one difference being that the method of the invention can only be used to measure and optimize subsea axial CP current (and current density), but not the long-line corrosion rate (which does not exist with subsea pipelines).

A further development results in significant savings if the CP system for a well casing can be cycled on and off, while the protection level would be measured by the ACMs.

In accordance with the present invention, a CP down hole axial current metering device is used to measure axial CP/corrosion current and to confirm and quantify the corrosive zones along a well casing. As a result, the invention can be used to determine the required CP current to protect these zones and to optimize the operation of the CP system.

The present invention is unique in the sense that it can be used in a wireless mode utilizing the coated casing as a communication medium between the ACMs and the MACM. Bare casings require a cable for communication.

Each ACM is a self-contained unit that collects and stores its measurement and then goes to sleep to minimize battery consumption, waiting for a signal from the MACM to transmit the data. The ACMs can be programmed to take measurements once a month, while the CP operator would only need to visit the site once a year to mount the MACM and collect the data from the downhole ACMs.

The downhole ACMs make direct electrical contact (by welded cables) to the metal sub. To the contrary, conventional logging tools measure axial current by establishing mechanical contact with the casing ID while the tool is being pulled from below the corrosive zone to above it. One limitation with existing tools is that the accuracy of the measurement is entirely governed by how successful the mechanical contact is made with the casing ID. This concern has been eliminated with the electrical connections provided by the device of the present invention.

Another advantage over existing tools is that the devices can be easily activated from the surface at any time without the need for specialized equipment or experienced personnel.

Each ACM used for practicing the method of the invention can be pre-assembled in the shop and made in the form of a self-contained sub that can be added to the casing as any other casing joint. This structure is compatible with the drilling operation requirements.

The present invention quantifies and confirms the location of corrosive zone(s) and the severity of corrosion in a new field by installing multiple units wherever there is thought to be a corrosive zone. In fields where the corrosive zones are identified from leaking history, this invention measures the axial corrosion current and helps design and optimize the CP system that will control this activity. It permits optimization of CP current to supply only the sufficient amount of current that will protect the deepest reachable corrosive zone.

These measurements can not be obtained with conventional logging, despite their high cost (e.g. approximately US $10,000 per log). Usually only one log, either static or polarized, is conducted on a selected well casing to determine the current requirement for the entire field and the information obtained from that log is generalized to other wells in the same field.

This invention makes it possible to confirm the corrosive zones in a new field and to determine and optimize the CP requirement for that field. In addition, it can be used to customize the protection level for six months in advance when the protective film has formed on the casing.

Significant savings can be realized through the application of "well engineered" CP current measurement for each well casing utilizing this invention.

While the disclosed method and apparatus have been particularly shown and described with respect to the preferred embodiments, it will be understood by those skilled in the art that various modifications in form and detail can be made therein without departing from the scope and spirit of the invention. Accordingly, modifications such as those suggested above, but not limited thereto, are to be considered within the scope of the invention, which is to be determined by reference to the following claims.

We claim:

1. A method of determining an amount of cathodic protection current to be applied to an underground metallic structure in contact with an underground earth formation, the structure having an extended underground length extending through a corrosive zone of the formation, with one end of the length being substantially near the earth's surface and another end of the length being below the corrosive zone, said method comprising the steps of:

mechanically connecting a first axial current meter (ACM) to the structure at a first underground depth substantially just above the corrosive zone for measuring a first axial current flowing through the structure at the first depth;

mechanically connecting a second axial current meter to the structure at a second underground depth substantially just below the corrosive zone for measuring a second axial current flowing through the structure at the second depth;

connecting a master axial current meter (MACM) to the structure substantially near the earth's surface;

operating the MACM over a selected limited time period to periodically obtain a series of first measurements of the first axial current from the first ACM and a series of second measurements of the second axial current from the second ACM, each second measurement being obtained at substantially the same time as a corresponding first measurement; and determining from the first and second measurements, an amount of cathodic protection current to be applied to the structure to avoid corrosion of the structure in the corrosive zone.

2. The method of claim 1, wherein the structure is a well casing.

3. The method of claim 2, wherein said step of mechanically connecting the first ACM to the well casing includes the step of mechanically connecting the first ACM to a first sub and the step of mounting the first sub on the well casing at the first depth.

4. The method of claim 2, wherein said step of mechanically connecting the second ACM to the well casing includes the step of mechanically connecting the second ACM to a second sub and the step of mounting the second sub on the well casing at the second depth.

5. The method of claim 2, wherein said step of operating the MACM occurs over approximately six months.

6. The method of claim 2, wherein each of the first and second ACMs is normally in an inactive state, wherein said step of operating the MACM includes the step of periodically remotely activating the first and second ACMs to measure the respective axial currents and to send the measurements to the MACM, and wherein each of the first and second ACMs returns to the inactive state after sending the respective measurement to the MACM.

7. The method of claim 6, wherein the well casing has a coating, and wherein said step of remotely activating includes the step of sending a respective activating signal through the coating to each of the first and second ACMs.

8. The method of claim 6, wherein the well casing is uncoated and has a cable extending from the MACM to each of the first and second ACMs, and wherein said step of remotely activating includes the step of sending a respective activating signal through the cable to each of the first and second ACMs.

9. The method of claim 1, wherein each of the first and second ACMs is normally in an inactive state, wherein said step of operating the MACM includes the step of periodically remotely activating the first and second ACMs to measure the respective axial currents and to send the measurements to the MACM, and wherein each of the first and second ACMs returns to the inactive state after sending the respective measurement to the MACM.

10. The method of claim 9, wherein the structure has a coating, and wherein said step of remotely activating includes the step of sending a respective activating signal through the coating to each of the first and second ACMs.

11. The method of claim 9, wherein the structure is uncoated and has a cable extending from the MACM to each of the first and second ACMs, and wherein said step of remotely activating includes the step of sending a respective activating signal through the cable to each of the first and second ACMs.

12. The method of claim 1, further comprising the steps of:

connecting a source of cathodic protection current between the structure and an anode bed; and applying the determined amount of cathodic protection current from the source to the structure.

13. An apparatus for determining an amount of cathodic protection current to be applied to an underground metallic structure in contact with an underground earth formation, the structure having an extended underground length extending through a corrosive zone of the formation, with one end of the length being substantially near the earth's surface and another end of the length being below the corrosive zone, said apparatus comprising:

a first axial current meter (ACM) mechanically connected to the structure at a first underground depth substantially just above the corrosive zone for measuring a first axial current flowing through the structure at the first depth;

a second axial current meter mechanically connected to the structure at a second underground depth substantially just below the corrosive zone for measuring a second axial current flowing through the structure at the second depth;

a master axial current meter (MACM) connected to the structure substantially near the earth's surface; and a connecting structure for carrying signals between said MACM and each of said first and second ACMs, wherein said MACM includes a control for operating over a selected limited time period to periodically obtain a series of first measurements of said first axial current from said first ACM and a series of second measurements of said second axial current from said second ACM, each second measurement being obtained at substantially the same time as a corresponding first measurement, and wherein said MACM provides information based on said first and second measurements for determining an amount of cathodic protection current to be applied to the structure to avoid corrosion of the structure in the corrosive zone.

14. The apparatus of claim 13, wherein the structure is a well casing.

15. The apparatus of claim 14, wherein said first ACM is mechanically connected to a first sub and said first sub is mounted on the well casing at the first depth.

16. The apparatus of claim 14, wherein said second ACM is mechanically connected to a second sub and said second sub is mounted on the well casing at the second depth.

17. The apparatus of claim 14, wherein said MACM is operated over approximately six months.

18. The apparatus of claim 14, wherein each of said first and second ACMs is normally in an inactive state, wherein said MACM periodically remotely activates said first and second ACMs to measure the respective axial currents and to send the measurements to said MACM, and wherein each of said first and second ACMs returns to the inactive state after sending the respective measurement to said MACM.

19. The apparatus of claim 18, wherein the well casing has a coating, and wherein said MACM sends a respective activating signal through the coating to each of said first and second ACMs.

20. The apparatus of claim 18, wherein the well casing is uncoated and has a cable extending from said MACM to each of said first and second ACMs, and wherein said MACM sends a respective activating signal through the cable to each of said first and second ACMs.

21. The apparatus of claim 13, wherein each of said first and second ACMs is normally in an inactive state, wherein said MACM periodically remotely activates said first and second ACMs to measure the respective axial currents and to send the measurements to said MACM, and wherein each of said first and second ACMs returns to the inactive state after sending the respective measurement to said MACM.

22. The apparatus of claim 21, wherein the structure has a coating, and wherein said MACM sends a respective activating signal through the coating to each of said first and second ACMs.

23. The apparatus of claim 21, wherein the structure has a cable extending from said MACM to each of said first and second ACMs, and wherein said MACM sends a respective activating signal through the cable to each of said first and second ACMs.

24. The apparatus of claim 13, further comprising a source of cathodic protection current connected between the structure and an anode bed, said source applying the determined amount of cathodic protection current to the structure.

* * * * *